(12) United States Patent
Chen

(10) Patent No.: US 6,215,406 B1
(45) Date of Patent: Apr. 10, 2001

(54) APPARATUS AND METHOD FOR DETECTING IGNITED FLAMMABLE GAS IN A CONDUIT

(75) Inventor: W. T. Chen, Hsin-Chu (TW)

(73) Assignee: Taiwan Semiconductor Manufacturing Co., Ltd, Hsin Chu (TW)

(*) Notice: Subject to any disclaimer, the term of this patent is extended or adjusted under 35 U.S.C. 154(b) by 0 days.

(21) Appl. No.: 09/483,217

(22) Filed: Jan. 14, 2000

(51) Int. Cl.$^7$ ..................................... G08B 17/10
(52) U.S. Cl. .................. 340/632; 340/577; 340/619; 364/496; 395/750
(58) Field of Search ....................... 340/632, 577, 340/619; 364/496; 395/750

(56) References Cited

U.S. PATENT DOCUMENTS

| | | | |
|---|---|---|---|
| 4,422,073 | * 12/1983 | Winner ........................... | 340/870.21 |
| 5,084,868 | * 1/1992 | Kelly et al. ........................ | 370/69.1 |
| 5,184,500 | * 2/1993 | Krcma et al. ....................... | 73/23.2 |
| 5,291,607 | * 3/1994 | Ristic et al. ....................... | 395/750 |
| 5,526,280 | * 6/1996 | Consadori et al. ................. | 364/496 |
| 5,786,768 | * 7/1998 | Chan et al. ........................ | 340/632 |

* cited by examiner

Primary Examiner—Daniel J. Wu
Assistant Examiner—Tai T. Nguyen
(74) Attorney, Agent, or Firm—Tung & Associates

(57) ABSTRACT

An apparatus and a method for detecting ignited flammable gas in a conduit or for detecting the impurity content of a gas composition are described. In the apparatus, a sensor body is provided which is equipped with at least one perforated isolator plate for slowing down the flow of an ignited flammable gas when fed back into the cavity of the detection apparatus. The sensor body further includes at least one optical sensor mounted juxtaposed to a gas inlet for sensing an ignited flammable gas and for sending a signal to a controller for shutting off the flammable gas supply. The present invention novel apparatus can further be utilized to detect the impurity level in a gas composition, and to detect any reaction product between a flammable gas and a material that forms the chamber component.

20 Claims, 4 Drawing Sheets

| | | VI | V2 | Action |
|---|---|---|---|---|
| Instruction | Normal Close | 11 | 11 | Deliver Gas |
| | OFF | 10 | 10 | Stop All Gas |
| | Normal Open | 00 | 00 | Deliver $N_2$ |

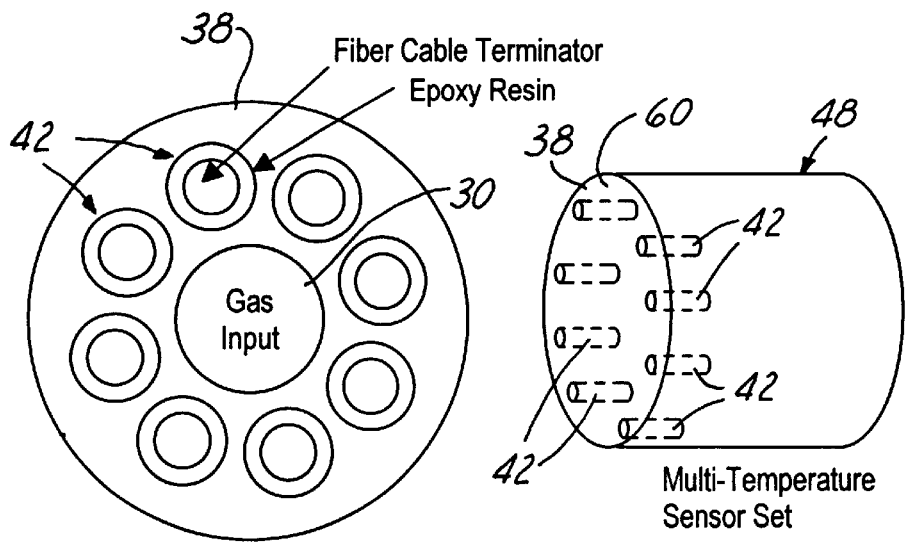
FIG. 4A    FIG. 4B
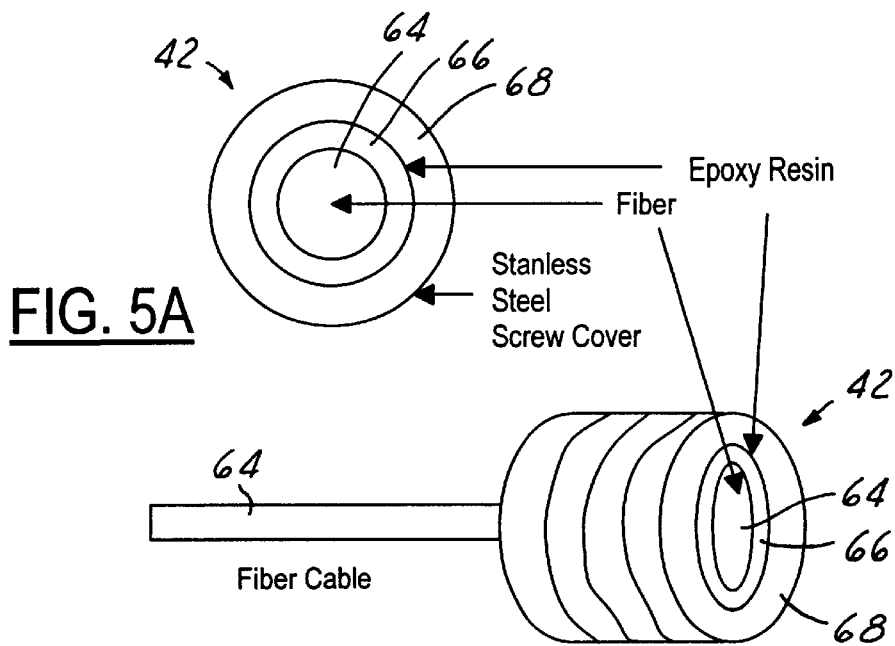
FIG. 5A
FIG. 5B

APPARATUS AND METHOD FOR DETECTING IGNITED FLAMMABLE GAS IN A CONDUIT

FIELD OF THE INVENTION

The present invention generally relates to an apparatus and a method for detecting an ignited flammable gas in a conduit connecting between a gas supply source and a semiconductor processing apparatus and more particularly, relates to an apparatus and a method for detecting ignited flammable gas in a conduit by using a multi-sensor module of fiber-optical sensors and at least one perforated isolator plate in a sensor body for the early detection of an ignited flammable gas.

BACKGROUND OF THE INVENTION

In the fabrication of semiconductor devices, a semiconducting wafer must be processed in a large number of processing steps for producing various integrated circuits on chips. These processing steps may amount to as many as several hundred. The various processing steps are conducted in a large variety of processing machines for carrying out chemical or physical reactions on the semi-conducting wafer. In the various fabrication steps, a large number of reactant gases are used. The reactant gases and their reaction products frequently encountered in the semiconductor fabrication industry may be highly flammable. For instance, the highly flammable gases may include silane, hydrogen and various other hydrocarbon gases. An effluent gas from the process machine must therefore be treated either in a chemical process or in a physical absorption or condensation process before it is released into a factory exhaust system and subsequently into the atmosphere.

The high flammability gases, which are normally of high boiling temperature or high boiling temperature components of other gases, present a serious processing hazard in the semiconductor fabrication facility. When such flammable gases are inadvertently, or accidentally ignited either in the chamber of a process machine or in a conduit connecting between the chamber and a flammable gas supply source, extremely serious consequences can result from such mishaps. Major fires have occurred in recent years in semiconductor fabrication facilities which result in serious personal injuries and equipment losses leading to a complete shutdown of the fabrication facility. The inadvertent or accidental ignition of a highly flammable gas can be caused by static electric charges, sparks produced by moving mechanical components or the self-igniting of flammable gases when exposed to high temperatures or oxygen environment.

The flammable gases that pose serious fire hazard may include those which are used as reactant gases and those which are by-products of a chemical reaction occurring in a reaction chamber. Since the exhaust conduits for the individual process machines are normally connected to a single factory exhaust, i.e., all the exhaust conduits from the various process machines are interconnected together in a fabrication facility, the spread of fire or explosion in the conduits can be extremely rapid and wide spread. For instance, a single fire started in a process machine can spread almost instantly to a large number of process machines and gas conveying conduits. The extent of damage to a semiconductor fabrication plant caused by a single fire started in a conduit or in a process machine can be astronomical as measured by the loss of human lives, bodily injuries and property damages.

After the occurrence of a fire in a fabrication facility, the recovery or clean-up procedure can be extremely laborious and time consuming. This is because the large amount of contaminating particles and debris generated during the fire which contaminates all the gas conveying conduits and the process chambers. It is not unusual that, after a major fire has erupted in a semiconductor fabrication facility, at least several months of production time is lost due to the clean-up and the refurbishing of damaged equipment.

It is therefore an object of the present invention to provide an apparatus and a method for detecting ignited flammable gas in a conduit or from a process machine that does not have the drawbacks and shortcomings of the conventional apparatus and methods.

It is another object of the present invention to provide an apparatus for detecting ignited flammable gas in a conduit by utilizing a sensor body equipped with at least one perforated isolator plate for slowing down the flow of an ignited flammable gas.

It is a further object of the present invention to provide an apparatus for detecting ignited flammable gas in a conduit by using a sensor body and at least one perforated isolator plate installed therein wherein both the body and the plate are fabricated of a corrosion-proof material.

It is another further object of the present invention to provide an apparatus for detecting ignited flammable gas in a conduit by using at least one fiber-optical sensor mounted at a gas inlet of a sensor body for sensing an ignited flammable gas in the cavity of the sensor body.

It is still another object of the present invention to provide an apparatus for detecting ignited flammable gas in a conduit by utilizing at least one fiber-optical sensor capable of detecting visible light, IR and UV emissions.

It is yet another object of the present invention to provide an apparatus for monitoring the composition of a gas in a conduit by using a sensor body equipped with at least one perforated isolator plate such that the flow of the gas can be slowed for detection by at least one optical sensor mounted at a gas inlet for the sensor body.

It is still another further object of the present invention to provide a method for detecting ignited flammable gas in a conduit by first providing a sensor body, flowing a flammable gas into the sensor body, mounting at least one optical sensor in the sensor body and sensing an ignited flammable gas in the cavity of the sensor body.

It is yet another further object of the present invention to provide a method for detecting ignited flammable gas in a conduit by first detecting an ignited flammable gas in a cavity of a sensor body by at least one optical sensor, and then sending a signal to a controller for stopping the flow of the flammable gas when ignited flammable gas is detected.

SUMMARY OF THE INVENTION

In accordance with the present invention, an apparatus and a method for detecting ignited flammable gas in a conduit are provided.

In a preferred embodiment, an apparatus for detecting ignited flammable gas in a conduit is provided which includes a sensor body of elongated cylindrical shape that has a gas inlet at one end for connecting to a gas supply source and a gas outlet at an opposite end for connecting to a process machine, at least one perforated isolator plate dividing a cavity in the sensor body forming at least two sub-cavities in the sensor body, the at least one perforated isolator plate slows down the propagation of an ignited flammable gas that feeds back into the sensor body through the gas outlet, and at least one optical sensor mounted at the gas inlet for sensing an ignited flammable gas in the cavity of the sensor body and for sending a signal to a controller for shutting off the gas source for the flammable gas.

In the apparatus for detecting ignited flammable gas in a conduit, the sensor body and the at least one perforated isolator plate may be fabricated of a substantially corrosion-proof material. The sensor body and the at least one perforated isolator plate may be fabricated of stainless steel. The at least one perforated isolator plate may include two isolator plates. The ignited flammable gas may be originated from the process machine or from a conduit connecting the sensor body to the process machine. The at least one optical sensor may be at least one fiber-optical sensor for detecting visible light, IR and UV emissions. The at least one perforated isolator plate may have circular holes with diameters between about 0.2 cm and about 2 cm. The at least one optical sensor may include a laser sensor for detecting the presence of particles in the cavity of the sensor body.

In another preferred embodiment, an apparatus for monitoring composition of a gas in a conduit is provided which includes a sensor body of elongated, cylindrical shape that has a gas inlet at one end for connecting to a gas supply source and a gas outlet at an opposite end for connecting to a process machine, at least one perforated isolator plate dividing a cavity in the sensor body forming at least two sub-cavities in the sensor body, and at least one optical sensor mounted juxtaposed to the gas inlet for sensing composition of a gas in the cavity of the sensor body and for sending a signal to a controller for determining action required when a deviation from specification is detected in the gas composition.

In the apparatus for monitoring composition of a gas in a conduit, the at least one perforated isolator plate slows down a flow rate of the gas in the cavity of the sensor body. The at least one optical sensor may include a laser sensor for detecting the presence of particles in the cavity of the sensor body. The sensor body and the at least one perforated isolator plate may be fabricated of a substantially corrosion-proof material. The at least one optical sensor may be at least one fiber-optic sensor for detecting visible light, IR and UV emissions. The at least one perforated isolator plate may have circular holes with diameters between about 0.2 cm and about 2 cm.

The present invention is further directed to a method for detecting an ignited flammable gas in a conduit that can be carried out by the operating steps of providing a sensor body of elongated, cylindrical shape that has a gas inlet at one end for connecting to a gas supply source and a gas outlet at an opposite end for connecting to a process machine, the sensor body has at least one perforated isolator plate that divides a cavity in the sensor body to form at least two sub-cavities in the sensor body, flowing a flammable gas into the gas inlet, through the cavity in the sensor body and out of the gas outlet for delivering to the process machine, mounting at least one optical sensor at the gas inlet, and sensing an ignited flammable gas in the cavity of the sensor body and sending a signal to a controller when the ignited flammable gas is detected.

The method for detecting ignited flammable gas in a conduit may further include the step of flowing a silane gas into the gas inlet, or the step of mounting at least one fiber-optical sensor at the gas inlet for detecting visible light, IR and UV emissions, or the step of mounting a laser sensor at the gas inlet for detecting solid particles. The method may further include the step of forming the at least one perforated isolator plate with holes that have diameters in the range between about 0.2 cm and about 2 cm. The method may further include the step of reducing a flow rate of the ignited flammable gas which enters the cavity in the sensor body through the gas outlet by the at least one perforated isolator plate.

BRIEF DESCRIPTION OF THE DRAWINGS

These and other objects, features and advantages of the present invention will become apparent from the following detailed description and the appended drawings in which:

FIG. 4A is a plane view of the gas inlet port of the present invention detection apparatus.

FIG. 4B is a perspective view of the present invention detection apparatus showing the placement of the optical sensors.

FIG. 5A is an end view of a fiber-optical sensor used in the present invention apparatus.

FIG. 5B is a perspective view of a fiber-optical sensor used in the present invention apparatus.

DETAILED DESCRIPTION OF THE PREFERRED EMBODIMENT

Figures 1, 2:
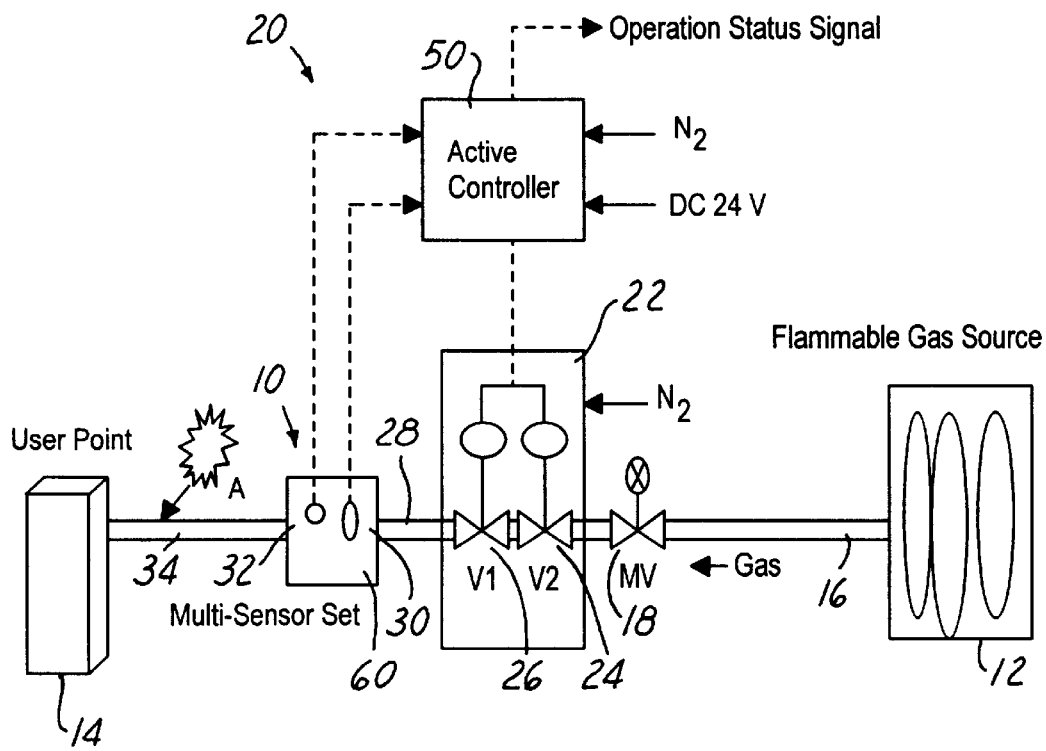
FIG. 1 is a graph illustrating a connection method of the present invention apparatus between a flammable gas supply source and a process machine.
FIG. 2 is a logic table illustrating the operation of two control valves for controlling a flow of flammable gas into the present invention detection apparatus.

The present invention discloses an apparatus and a method for detecting ignited flammable gas in a conduit that connects between a flammable gas supply source and a process equipment. The detection apparatus is constructed of a sensor body of elongated, cylindrical shape defining a cavity therein. The cavity is divided into at least two sub-cavities by at least one perforated isolator plate mounted inside the cavity for slowing down the flow rate of an ignited flammable gas or any other gas composition to be analyzed. The perforated isolator plate is normally equipped with apertures of any suitable shape. When the apertures are provided in circular holes, a suitable diameter of the holes is between about 0.2 cm and about 2 cm. The detection apparatus is further equipped with at least one optical sensor, and usually equipped with 6~8 optical sensors that are mounted at a gas inlet port of the sensor body for sensing the presence of an ignited flammable gas, or the concentration of certain impurities in a gas composition that is flown into the cavity of the sensor body. The at least one optical sensor may be supplied in fiber-optical sensors or laser sensors. The fiber-optical sensors are suitable for detecting spectrum of light such as visible light, infrared and ultraviolet emissions. The laser sensor is more suitable for detecting the presence and the concentration of particles in the gas content in the cavity of the sensor body. An improved detection by a broader coverage of the emission spectrum and particles can be accomplished by a combination used of the fiber-optical sensors and the laser sensors.

In a preferred embodiment, the present invention novel detection apparatus is used to advantageously detect an ignited flammable gas in a conduit that connects between a flammable gas supply source and a process machine. The light spectrum produced by the ignition of the flammable gas can be suitably detected by the fiber-optical sensors equipped in the sensor body. Furthermore, during the ignition and burning of the flammable gas, considerable amount of particles, including that of carbon are produced. These particles can be advantageously detected by the laser sensor. When an ignited flammable gas is detected in the conduit, a signal is sent out to a logic controller through an amplifier and a logic set, a second signal is then sent out to an active controller which shuts off the supply of the flammable gas into the system. The continuing ignition of the flammable gas can thus be stopped after the amount of flammable gas existed in the conduit is completely consumed by the ignition or burning.

In another preferred embodiment, the present invention novel detection apparatus can be used advantageously for detecting the presence of an amount of impurity in a process gas composition that is in the conduit. When an unusual amount, i.e., exceeding that of the specification limit is detected, a signal is sent out to a logic controller and then to an active controller for alerting the machine operator of the improper process condition. This prevents the use of a process gas that contains an extraordinary amount of impurity and thus the production of sub-standard IC chips.

The present invention further provides a method for detecting the presence of an ignited flammable gas in a conduit that connects between a flammable gas supply source and a process machine. The method can be carried out by first providing a sensor body that is equipped with at least one perforated isolator plate, a gas inlet and a gas outlet. The at least one perforated isolator plate serves the function of slowing down the flow of gas through the sensor body, including possibly an ignited flammable gas that back flows into the sensor body through the gas outlet. When the step of sensing an ignited flammable gas in the cavity of the sensor body is confirmed, a signal is sent out by the fiber-optical sensor to a logic controller and an active controller for shutting off the supply of the flammable gas and thus preventing further propagation of the fire. The present invention novel method can be suitably used to detect any ignited flammable gas such as silane, hydrogen or other flammable hydrocarbon gases.

Figure 3:
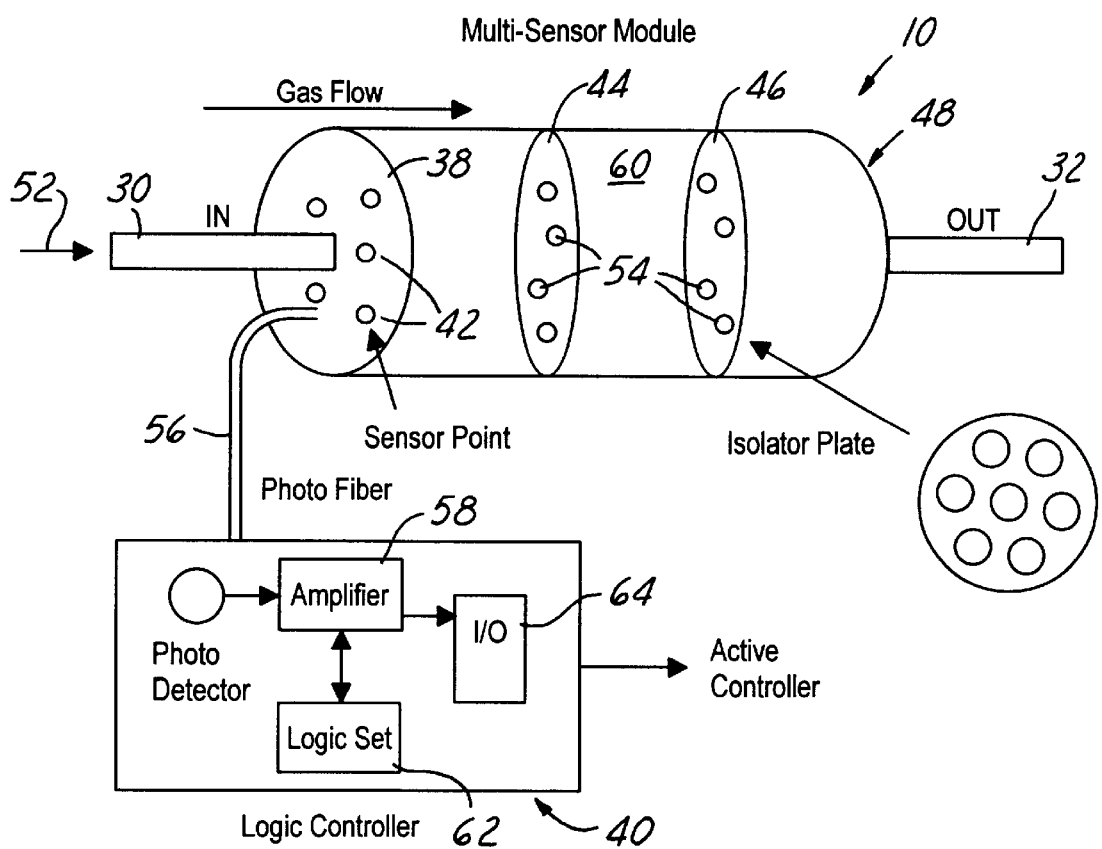
FIG. 3 is a partially cut-out, perspective view of the present invention apparatus for detecting ignited flammable gas.

Referring initially to FIG. 1, wherein a present invention novel detection apparatus 10 is shown in a fabrication system 20 which connects a flammable gas supply source 12 and a process machine 14. The flammable gas supply source 12 may consist of a plurality of gas storage cylinders that are parallely connected to supply a flammable gas through conduit 16 and flow control valve 18 into a valve manifold box 22. Inside the valve manifold box 22 is equipped with logic circuit control valves 24 and 26. The flammable gas enters the detection apparatus 10 through inlet 30 and conduit 28. A detailed drawing illustrating the construction of the detection apparatus 10 is shown in FIG. 3. The flammable gas flows through the detection apparatus 10 through a gas outlet 32 and conduit 34 into the process machine 14. The flammable gas flows into the detection apparatus 10 through an inlet valve 30. The present invention detection apparatus 10 includes a logic controller 40 (shown in FIG. 3) which controls an active controller 50 for shutting off the flammable gas supply conduit when an ignited flammable gas is detected in conduit 34, i.e., when the ignited flammable gas propagates from conduit 34, through gas outlet 32 into the detection apparatus 10.

The logic operation of the valve manifold box 22 which contains shut off valves 24, 26 is shown in FIG. 2. It is seen that when the valves 24, 26 are in normal close position, a flammable gas is delivered through conduit 28 into the detection apparatus 10. When both the shut off valves 24, 26 are in an off position, all gas flow through the valve manifold box 22 is stopped. When the valves 24, 26 are in normal open position, an inert purge gas of nitrogen is delivered through the valve manifold box 22 into the detection apparatus 10.

A partially cut-out, perspective view of the present invention detection apparatus 10 is shown in FIG. 3. The multi-sensor apparatus 10, i.e., with five optical sensors 42 shown, is equipped with two perforated isolator plates 44, 46. The sensor body 48 further includes a gas inlet 30 and a gas outlet 32. During normal operation, a flammable gas 52 such as silane, is fed into the gas inlet 30 and flows through apertures 54 in the isolator plates 44, 46 into the gas outlet 32 for use in a process machine 14 (shown in FIG. 1). When a fire is detected in the conduit 34 (shown in FIG. 1) juxtaposed to the gas outlet 32, the ignited flammable gas feeds back through outlet 32 into the cavity 60 of the sensor body 48. The ignited flammable gas normally travels at a high flow rate due to its nature of a turbulent flow and its reaction dynamics. The perforated isolator plates 44, 46 slow down the flow rate of the ignited flammable gas such that the plurality of optical sensors 42 can be used to detect its presence. After the ignited flammable gas is detected, a signal is sent to the logic controller 40 through a fiber-optical cable 56. The logic controller 40 is further equipped with an amplifier 58, a logic set 62 and an input/output device 64 for outputting a signal to the active controller 50 (shown in FIG. 1). Instead of the fiber-optical sensors 42, a laser sensor (not shown) can be similarly mounted juxtaposed to the gas inlet 30 for detecting particles in cavity 60 of the sensor body 48.

A plane view of the inlet plate 38 wherein the plurality of fiber-optical sensors 42 are mounted is shown in FIG. 4A. FIG. 4B is a perspective view of the sensor body 48 illustrating the positions of the sensors 42 which are mounted in the mounting plate 38. It should be noted that while eight fiber-optical sensors 42 are shown in FIGS. 4A and 4B, any other suitable number or combination of fiber-optical sensors 42 and laser sensors (not shown) can be mounted in the sensor mounting plate 38 for detecting either an ignited flammable gas or an impurity content of a gas composition in the cavity 60 of the sensor body 48.

The construction of the fiber-optical sensors 42 is shown in FIGS. 5A and 5B in a plane view and a perspective view, respectively. As shown in FIG. 5A, the fiber optical sensor 42 is constructed by a fiber glass core 64, an epoxy resin coating 66 and a stainless steel cover 68. It should be noted that FIGS. 5A ad 5B merely illustrate one possibly fiber-optical sensor construction, any other suitable fiber-optical sensors, or any other optical sensors or laser sensors can be suitably used in the present invention novel detection apparatus 10. The optical sensors are more suited for detecting optical spectra of visible light, infrared light or ultraviolet light, while laser sensors are more effective in detecting the presence or concentration of solid particles in a gas.

The sensor body 48, the perforated isolator plates 44, 46 and the sensor mounting plate 38 can be fabricated in a material that is substantially corrosion-proof. One of such suitable material is stainless steel. However, any other suitable material such as a Teflon coated metal may also be used. The size of the apertures 54 in the isolator plates 44, 46 can be of any suitable size, one frequently used size is approximately ⅛ of the diameter of the sensor body 48. Frequently used aperture size may be between about 0.2 cm and about 2 cm.

The present invention novel detection apparatus 10 can be utilized not only for detecting ignited flammable gas, but also for detecting impurity content in a gas composition or the presence of any reaction product generated between the flammable gas and the sensor body material. Since flammable gases are normally of corrosive nature, chemical reactions with the sensor body components have frequently been observed.

Figure 6:
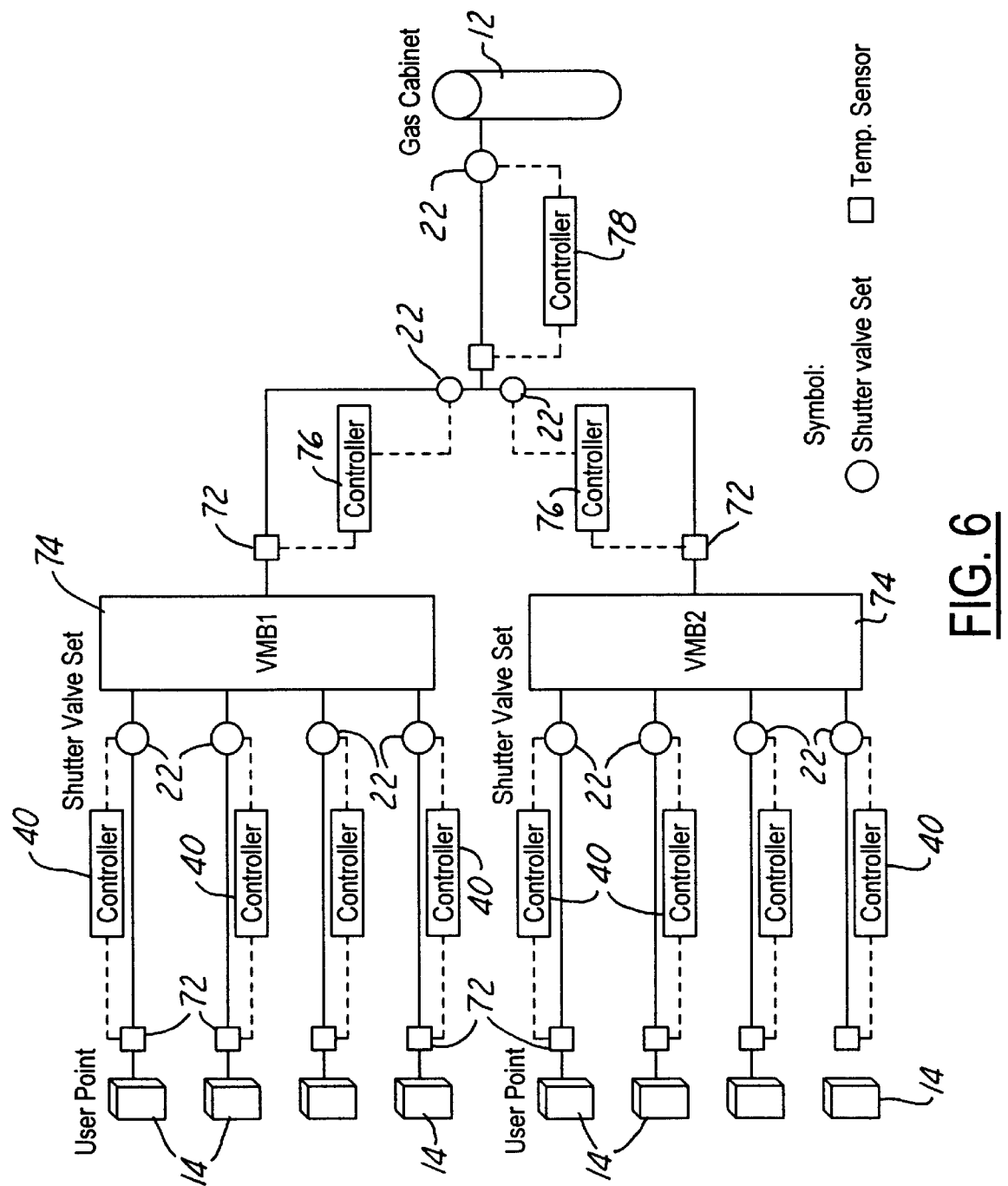
FIG. 6 is a flow chart for using the present invention detection apparatus when a single gas supply source is used to feed a multiple number of process machines.

The present invention novel detection apparatus 10 can further be used in a multiple process machine system, as shown in FIG. 6, wherein a multiple number of logic controllers 40 are utilized to control a multiple number of process machines 14 through a temperature sensor 72 mounted on each process machine in fluid communication with the process machine cavity. The logic controller is further connected to valve manifold boxes 22 and subsequently to a valve control bank 74. Through a series of other controllers 76, 78, the gas conduit is connected to the gas cabinet 12 for supplying a flammable gas.

The operation of the present invention novel detection apparatus 10 can be described according to FIG. 1. During normal operation (without ignited flammable gas detected), the flammable gas is fed from the flammable gas supply source 12 into conduit 16 through the manual control valve 18. The flammable gas is then fed through the valve manifold box 22 through control valves 24, 26. The flammable gas is then fed through conduit 28 into a gas inlet 30 of the detection apparatus 10. The multi-sensor utilized in the apparatus 10 does not detect any ignited flammable gas, so that the flammable gas is fed into the process machine 14 (or the user point).

When a fire has occurred in the conduit 34, or the presence of an ignited flammable gas is detected, the flame propagates through conduit 34 into a temperature sensor in the detection apparatus 10. Since the ignited flammable gas enters a large cavity 60 of the sensor body 48, the burning of the flammable gas becomes more efficient with the available space for burning. The temperature of the cavity 60 gradually increases due to the burning of the flammable gas. The temperature sensor 72 (not shown in FIG. 1) then activates the logic controller 40 for sending out a signal to the active controller 50 to shut off the conduit and thus stopping the flammable gas supply. After the flammable gas supply line is shut off, an inert gas such as nitrogen is fed into the conduit 28, the cavity 60 and the conduit 34 to stop the flammable gas from burning. An alarm signal is sent simultaneously to the control panel of the process machine to alert the machine operator for initiating emergency response actions.

The present invention novel detection apparatus and a method for using such apparatus have therefore been amply described in the above descriptions and in the appended drawings of FIGS. 16.

While the present invention has been described in an illustrative manner, it should be understood that the terminology used is intended to be in a nature of words of description rather than of limitation.

Furthermore, while the present invention has been described in terms of a preferred embodiment, it is to be appreciated that those skilled in the art will readily apply these teachings to other possible variations of the inventions.

The embodiment of the invention in which an exclusive property or privilege is claimed are defined as follows:

1. An apparatus for detecting ignited flammable gas in a conduit comprising:
    a sensor body of elongated, cylindrical shape having a gas inlet at one end for connecting to a gas supply source and a gas outlet at an opposite end for connecting to a process machine,
    at least one perforated isolator plate dividing a cavity in said sensor body forming at least two sub-cavities in said sensor body, said at least one perforated isolator plate slows down the propagation of an ignited flammable gas that feeds back into said sensor body through said gas outlet, and
    at least one optical sensor mounted at said gas inlet for sensing an ignited flammable gas in the cavity of said sensor body and for sending a signal to a controller for shutting off said gas source for said flammable gas.

2. An apparatus for detecting ignited flammable gas in a conduit according to claim 1, wherein said sensor body and said at least one perforated isolator plate are fabricated of a substantially corrosion-proof material.

3. An apparatus for detecting ignited flammable gas in a conduit according to claim 1, wherein said sensor body and said at least one perforated isolator plate are fabricated of stainless steel.

4. An apparatus for detecting ignited flammable gas in a conduit according to claim 1, wherein said at least one perforated isolator plate comprises two isolator plates.

5. An apparatus for detecting ignited flammable gas in a conduit according to claim 1, wherein said ignited flammable gas being originated from said process machine or from a conduit connecting said sensor body and said process machine.

6. An apparatus for detecting ignited flammable gas in a conduit according to claim 1, wherein said at least one optical sensor being at least one fiber-optical sensor for detecting visible light, IR and UV emissions.

7. An apparatus for detecting ignited flammable gas in a conduit according to claim 1, wherein said at least one perforated isolator plate having circular holes with diameters between about 0.2 cm and about 2 cm.

8. An apparatus for detecting ignited flammable gas in a conduit according to claim 1, wherein said at least one optical sensor comprises a laser sensor for detecting the presence of particles in said cavity of the sensor body.

9. An apparatus for monitoring composition of a gas in a conduit comprising:
    a sensor body of elongated, cylindrical shape having a gas inlet at one end for connecting to a gas supply source and a gas outlet at an opposite end for connecting to a process machine,
    at least one perforated isolator plate dividing a cavity in said sensor body forming at least two sub-cavities in said sensor body, and
    at least one optical sensor mounted juxtaposed to said gas inlet for sensing composition of a gas in said cavity of the sensor body and for sending a signal to a controller for determining action required when a deviation from specification is detected in said gas composition.

10. An apparatus for monitoring composition of a gas in a conduit according to claim 9, wherein said at least one perforated isolator plate provided slows down flow rate of said gas in the cavity of the sensor body.

11. An apparatus for monitoring composition of a gas in a conduit according to claim 9, wherein said at least one perforated isolator plate having circular holes with diameters between about 0.2 cm and about 2 cm.

12. An apparatus for monitoring composition of a gas in a conduit according to claim 9, wherein said sensor body and said at least one perforated isolator plate are fabricated of a substantially corrosion-proof material.

13. An apparatus for monitoring composition of a gas in a conduit according to claim 9, wherein said at least one optical sensor being at least one fiber-optical sensor for detecting visible light, IR and UV emissions.

14. An apparatus for monitoring composition of a gas in a conduit according to claim 9, wherein said at least one perforated isolator plate having circular holes with diameters between about 0.2 cm and about 2 cm.

15. A method for detecting ignited flammable gas in a conduit comprising the steps of:

providing a sensor body of elongated, cylindrical shape having a gas inlet at one end for connecting to a gas supply source and a gas outlet at an opposite end for connecting to a process machine, said sensor body having at least one perforated isolator plate dividing a cavity in said sensor body forming at least two sub-cavities in said sensor body, flowing a flammable gas into said gas inlet, through said cavity in said sensor body and out of said gas outlet for delivering to said process machine, mounting at least one optical sensor at said gas inlet, and sensing an ignited flammable gas in the cavity of said sensor body and sending a signal to a controller when said ignited flammable gas is detected.

16. A method for detecting ignited flammable gas in a conduit according to claim 15 further comprising the step of flowing a silane gas into said gas inlet.

17. A method for detecting ignited flammable gas in a conduit according to claim 15 further comprising the step of mounting at least one fiber-optical sensor at said gas inlet for detecting visible light, IR and UV emissions.

18. A method for detecting ignited flammable gas in a conduit according to claim 15 further comprising the step of mounting a laser sensor at said gas inlet for detecting solid particles.

19. A method for detecting ignited flammable gas in a conduit according to claim 15 further comprising the step of forming said at least one perforated isolator plate with holes having diameters in the range between about 0.2 cm and about 2 cm.

20. A method for detecting ignited flammable gas in a conduit according to claim 15 further comprising the step of reducing a flow rate of said ignited flammable gas which enters said cavity in the sensor body through said gas outlet by said at least one perforated isolator plate.

* * * * *